United States Patent [19]

Jaffe et al.

[11] Patent Number: 5,067,942
[45] Date of Patent: Nov. 26, 1991

[54] SINGLE USE HYPODERMIC NEEDLE

[75] Inventors: Richard A. Jaffe, Palo Alto; A. Christopher Allison, Pacifica, both of Calif.

[73] Assignee: The Board of Trustees of the Leland Stanford Junior University, Palo Alto, Calif.

[21] Appl. No.: 632,088

[22] Filed: Dec. 20, 1990

[51] Int. Cl.$^5$ ............................................. A61M 5/00
[52] U.S. Cl. ..................................... 604/110; 604/240; 604/215
[58] Field of Search ............... 604/110, 111, 188, 225, 604/239–241, 65, 242, 243, 167, 171, 199, 201–207, 215, 236, 264, 87

[56] References Cited

U.S. PATENT DOCUMENTS

| | | | |
|---|---|---|---|
| 2,841,143 | 7/1958 | Bertram | 604/241 |
| 3,523,533 | 8/1970 | Burke | 604/240 |
| 3,895,633 | 7/1975 | Bartner et al. | 604/241 |
| 4,233,975 | 11/1980 | Yerman | 604/110 |
| 4,404,862 | 9/1983 | Harris, Sr. | 604/241 |
| 4,770,655 | 9/1988 | Haber et al. | 604/110 |
| 4,828,547 | 5/1989 | Saki et al. | 604/110 |
| 4,923,443 | 5/1990 | Greenwood et al. | 604/110 |
| 4,935,041 | 6/1990 | Haber | 604/110 |
| 4,978,340 | 12/1990 | Terrill et al. | 604/110 |
| 4,984,580 | 1/1991 | Wanamaker | 604/240 |

FOREIGN PATENT DOCUMENTS 2215613  9/1989  United Kingdom ............... 604/110

Primary Examiner—C. Fred Rosenbaum
Assistant Examiner—Sharon Finkel
Attorney, Agent, or Firm—Townsend and Townsend

[57] ABSTRACT

A single use needle assembly includes a needle extending through a base with a hub extending from the base for engaging a syringe. The end of the needle within the hub has a port which is covered by a retractable sheath. When the needle assembly and a syringe are assembled, two separable tabs held within a basket force the sheath to retract and expose the port in the needle whereby a fluid can flow through the needle. Upon disassembly of the needle syringe, the tabs separate from the basket and are effectively destroyed for further use in retracting the sheath.

8 Claims, 3 Drawing Sheets

SINGLE USE HYPODERMIC NEEDLE

This application is related to copending application Ser. No. 07/390,083, now abandoned, filed Aug. 7, 1989 for "Insertable Element for Preventing Reuse of Plastic Syringe."

BACKGROUND OF THE INVENTION

This invention relates generally to hypodermic needles and syringes, and more particularly the invention relates to a single use hypodermic needle.

The safe disposal of hypodermic needles is a concern in the medical and health care professions especially in view of the desire for needles by intravenous drug users. The multiple use of needles is known to transmit diseases among the users and is a major factor in the spread of AIDS.

The present invention is directed to a hypodermic needle which can be used only once. Accordingly, the needle cannot be used by multiple users, thereby reducing the spread of disease.

SUMMARY OF THE INVENTION

An object of the invention is a single use hypodermic needle.

A feature of the invention is a needle having a port in one end with a sheath retractably covering the port.

Another feature of the invention is means for retracting a sheath and exposing an access port in a needle whereby the retracting means is effectively destroyed after one use.

The invention and objects and features thereof will be more readily apparent from the following detailed description and appended claims when taken with the drawings.

DETAILED DESCRIPTION OF ILLUSTRATIVE EMBODIMENTS

Figure 1A:
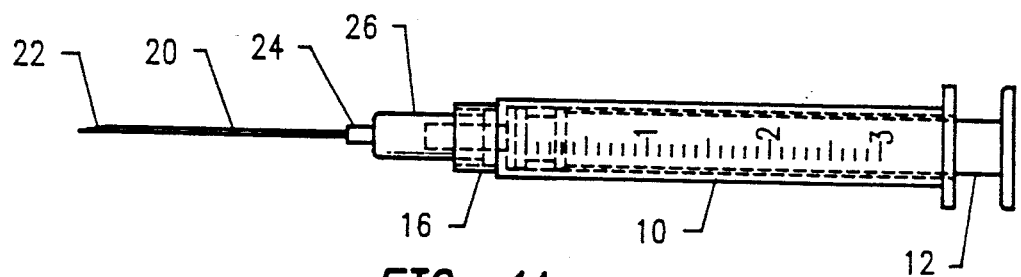
FIG. 1A and FIG. 1B are side elevation views of a conventional hypodermic needle and syringe assembled and disassembled, respectively.
Figure 1B:
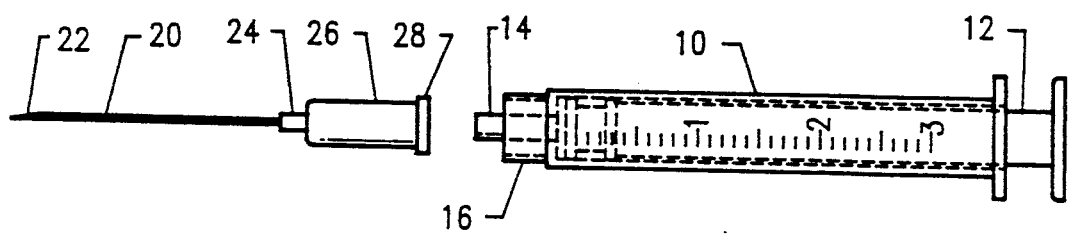

Referring now to the drawing, FIG. 1A and FIG. 1B are side views of a conventional needle and syringe as assembled and as disassembled, respectively. The syringe includes a housing 10 having an open end through which a plunger 12 is inserted into the housing. The opposing end of the housing 10 includes a Luer tip 14 having an opening there through for communicating with the housing 10. Surrounding the Luer tip 14 is an outer Luer threaded cylindrical wall 16. The wall is optional and comprises a Luer lock assembly.

The needle assembly includes a needle 20 having a sharpened end 22 and an opposing end which extends through a plastic or metal base 24. A hub 26 extends from the base 24 and includes a lip 28 for threadibly engaging the outer wall 16 around the Luer tip 14. Alternatively, the hub 26 can engage the Luer tip in a press fit.

Heretofore, the needle assembly has been capable of multiple uses, and the needle assembly must be physically destroyed to prevent reuse of the needle assembly. However, destruction of the needles require special handling and equipment, and often times the needles are merely discarded.

Figure 2A:
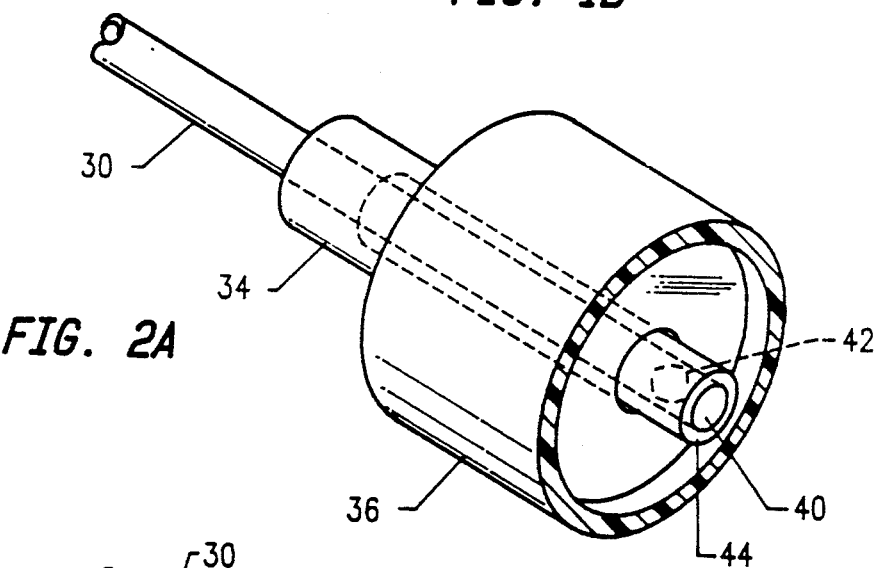
FIG. 2A and FIG. 2B are perspective views of a needle assembly in accordance with one embodiment of the invention.
Figure 2B:
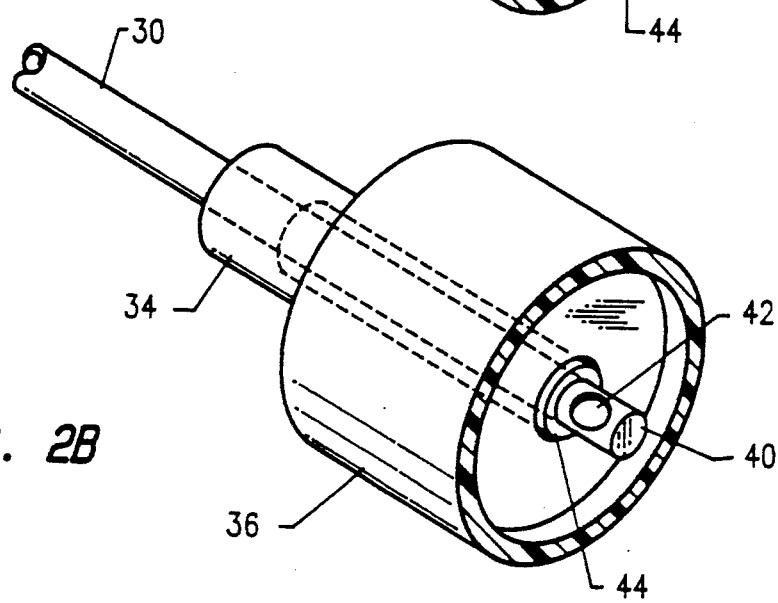

The present invention is directed to a needle assembly having a single use. FIG. 2A and FIG. 2B are perspective views illustrating one embodiment of the needle assembly. In this embodiment a needle 30 extends through a base 34 within a hub 36 (shown partially removed for illustration purposes). The end 40 of needle 30 within hub 36 is closed, and a port 42 is provided through the sidewall of the needle. A retractable sheath such as a silicone rubber tube 44 covers the needle and port 42, as shown in FIG. 2A. However, means is provided within the hub for forcing the sheath to retract when the needle and syringe are assembled. Importantly, the means which retracts the sheath is effectively destroyed after one use thereby rendering the needle unusable after the first use.

Figure 3A:
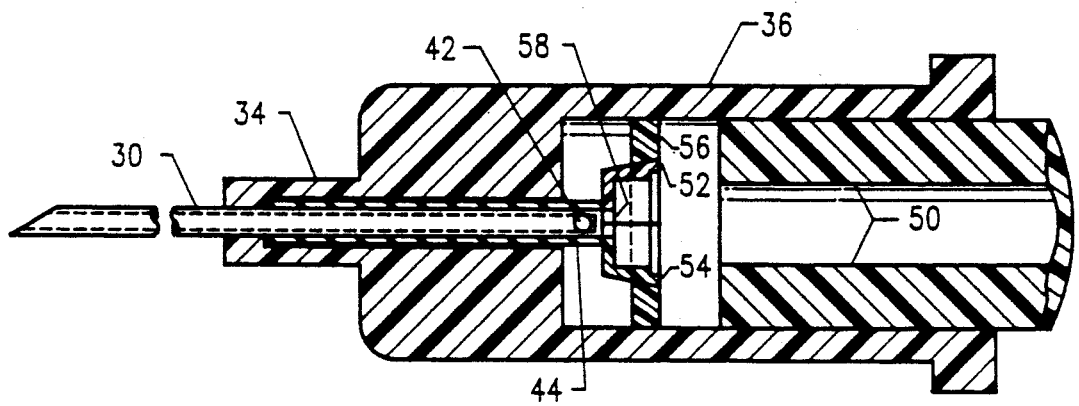
FIGS. 3A, 3B, and 3C are side views in section illustrating the use of the needle assembly of FIGS. 2A, 2B.
Figure 3B:
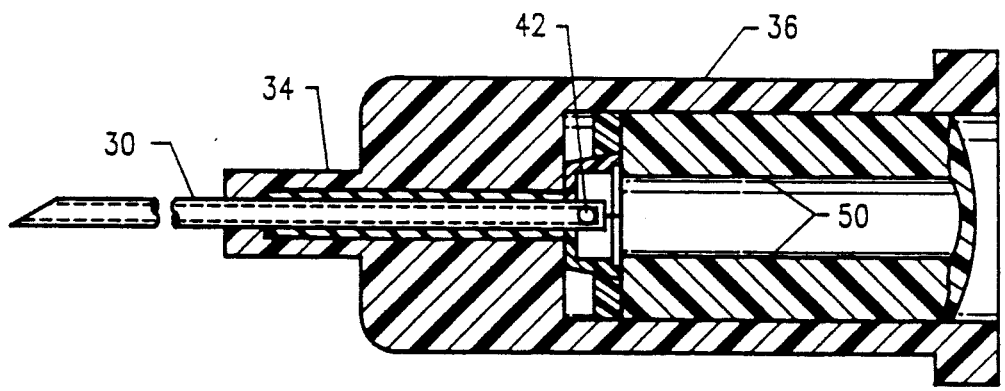
Figure 3C:
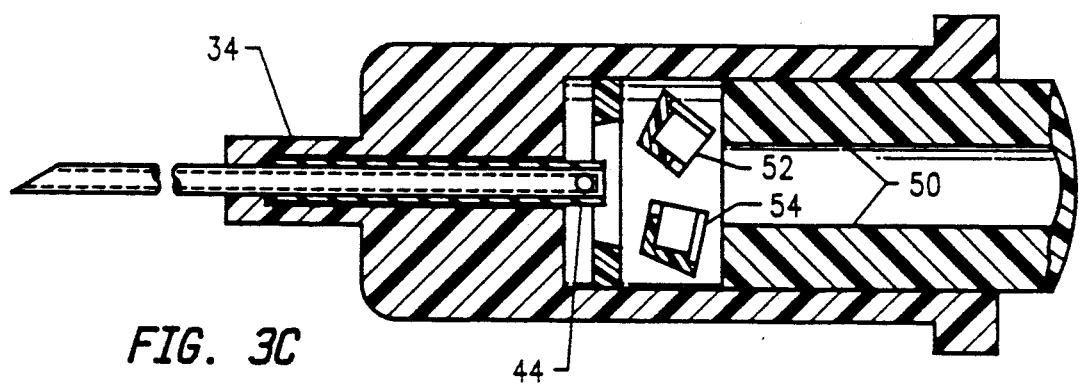

FIGS. 3A, 3B, and 3C are side views in section illustrating the use of the needle assembly of FIGS. 2A and 2B. In FIG. 3A the needle assembly is being assembled to a syringe by force fit of the hub 36 on Luer tip 50 of the syringe. Positioned within the hub 36 are two tabs 52, 54 which are held together in a basket 56. The forward end of the tabs define a hole 58 through which the needle can pass, with the ends of the tabs engaging the sheath 44. As the Luer tip 50 engages the tabs 52, 54 and basket 56, the sheath is retracted thereby exposing the port 42 in the needle as shown in FIG. 3B. At this time a fluid from the syringe can pass through the Luer tip and into the needle through the port 42. The ring or basket 56 is repositioned in a forced fit in the hub 36.

After use, the needle and the syringe are disassembled, and the tabs 52, 54 are pushed from the basket 56 by the force of the sheath, thereby effectively destroying the tabs for further use. The sheath again covers the port and prevents further use of the needle.

Figure 4A:
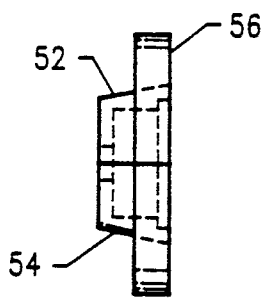
FIGS. 4A, 4B, and 4C are side views of a basket and retaining tabs illustrating operation thereof in the needle assembly of FIGS. 3A-3C.
Figure 4B:
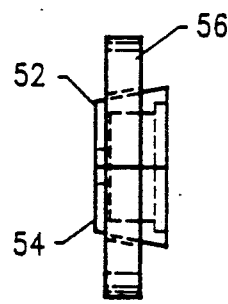
Figure 4C:
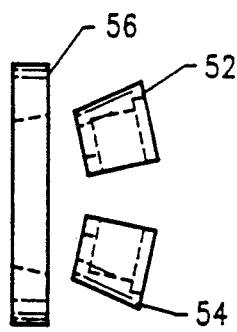

FIGS. 4A-4C are side views of the basket and retaining tabs of FIGS. 3A, 3B further illustrating operation thereof. In FIG. 4A the tabs 52, 54 are assembled in the basket 56 which comprises an annular body having a tapered hole therethrough. Each of the tabs has a tapered outer surface which mates with the tapered hole of the basket. In FIG. 4B after the syringe is disassembled from the needle, the sheath exerts pressure on the tabs thereby dislodging tabs from the basket 56. In FIG. 4C the two tabs are completely expelled from the basket and separate from each other. Due to the small sizes of the tabs, the repositioned basket and tabs are not readily reassembled. Further manual replacement of the basket and tabs within the hub 36 is nearly impossible due to the forced fit of the repositioned basket in the hub.

Figure 5A:
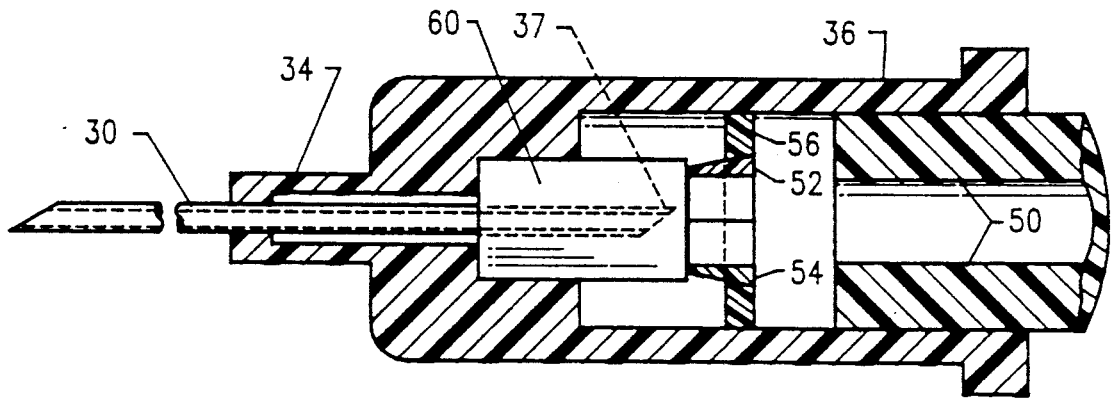
FIGS. 5A, 5B, and 5C are side views in section illustrating a needle assembly in accordance with another embodiment of the invention.
Figure 5B:
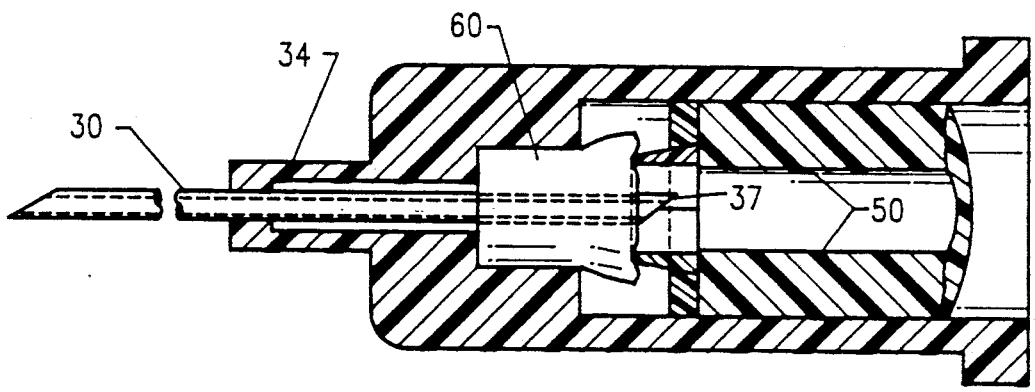
Figure 5C:
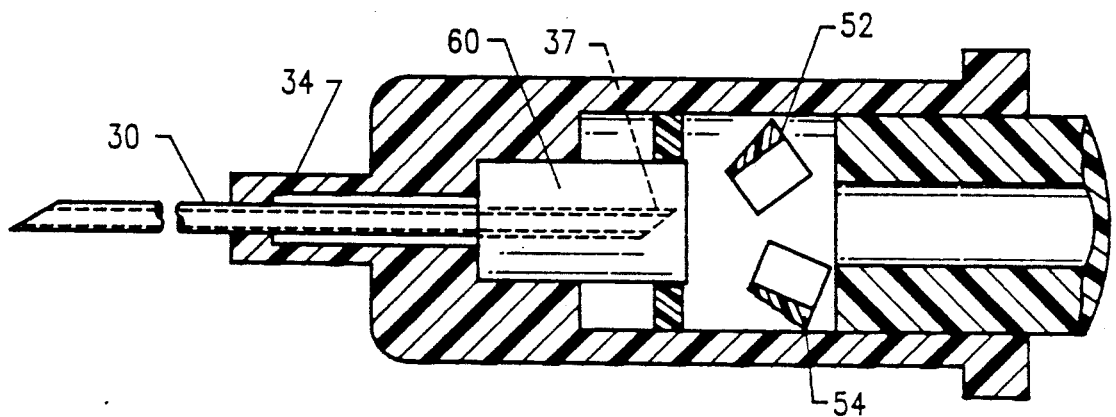

FIGS. 5A-5C are side views in section illustrating a needle assembly in accordance with another embodiment of the invention. Like elements in FIGS. 3 and 5 have the same reference numerals. In this embodiment the end of needle 30 within hub 36 is sharpened as shown at 37, and the portion of the needle within hub 36 is encapsulated in a solid flexible silicone rubber block 60. As shown in FIG. 5B, assembly of the syringe and the needle causes the tabs 52, 54 to exert pressure on the rubber block 60 thereby exposing the open end 37 of the needle and permitting fluid from the syringe to pass through the needle. In FIG. 5C the syringe is disassembled from the needle whereupon the tabs are again expelled from the basket 56 by the force of the rubber block 60, and the separated tabs are no longer useful in retracting the solid rubber block sheath.

There has been described several embodiments of a single use hypodermic needle and syringe assembly. While the invention has been described with reference to specific embodiments, the description is illustrative of the invention and is not to be construed as limiting the invention. Various modifications and applications may occur to those skilled in the art without departing from the true spirit and scope of the invention as defined by the appended claims.

We claim:

1. In combination, a needle and syringe assembly comprising
    a syringe having a cylindrical housing with a first open end, a plunger extending into said housing through said open end, and a second end having a Luer tip including a passage communicating with said housing;
    a needle including a needle having a sharpened first end and a second end with at least one port through said needle near said second end, a base through which said needle extends, a hub extending from said base for engaging said syringe, and a sheath retractably covering said at least one port, and means in said syringe for retracting said sheath when said syringe and needle are assembled, said means being effectively destroyed upon disassembly of said syringe and needle, and said sheath again covering said port upon disassembly of said syringe and needle thereby preventing re-use of said needle.

2. The combination as defined by claim 1 wherein said second end of said needle is closed and said sheath comprises a flexible tube around said needle and covering said port.

3. The combination as defined by claim 2 wherein said means for retracting said sheath comprises two separable tabs and basket for holding said tabs together.

4. The combination as defined by claim 3 wherein said basket comprises an annular body having a tapered hole there through, said tabs having tapered surfaces for mating with said tapered hole.

5. The combination as defined by claim 1 wherein said sheath comprises a solid flexible block encapsulating said second end.

6. The combination as defined by 5 wherein said second end is sharpened.

7. The combination as defined by claim 5 wherein said means for retracting said sheath comprises two separable tabs and a basket for holding said tabs together.

8. The combination as defined by claim 7 wherein said basket comprises an annular body having a tapered hole there through, said tabs having tapered surfaces for mating with said tapered hole.

* * * * *